United States Patent
Voigtsberger et al.

(10) Patent No.: US 9,034,225 B2
(45) Date of Patent: May 19, 2015

(54) PROCESS FOR PRODUCING IMPLANTS AND COMPONENTS BY DIRECTING SHAPING

(75) Inventors: Baerbel Voigtsberger, Bad Klosterlausnitz (DE); Martina Johannes, Hermsdorf (DE); Helke Rudolph, Eurasburg (DE); Ralph Gunnar Luthardt, Ulm (DE)

(73) Assignee: Fraunhofer-Gesellschaft zur Foerderung de angwandten Forschung e. V, Munich (DE)

( * ) Notice: Subject to any disclaimer, the term of this patent is extended or adjusted under 35 U.S.C. 154(b) by 691 days.

(21) Appl. No.: 12/673,101

(22) PCT Filed: Aug. 13, 2008

(86) PCT No.: PCT/DE2008/050026
§ 371 (c)(1),
(2), (4) Date: Aug. 12, 2010

(87) PCT Pub. No.: WO2009/021510
PCT Pub. Date: Feb. 19, 2009

(65) Prior Publication Data
US 2011/0127001 A1    Jun. 2, 2011

(30) Foreign Application Priority Data
Aug. 15, 2007 (DE) .......................... 10 2007 038 958

(51) Int. Cl.
*A61C 13/00* (2006.01)
*A61C 8/00* (2006.01)

(52) U.S. Cl.
CPC .......... *A61C 13/0003* (2013.01); *A61C 8/0012* (2013.01)

(58) Field of Classification Search
CPC .................................................. A61C 13/0003
USPC .............................................................. 264/16
See application file for complete search history.

(56) References Cited

U.S. PATENT DOCUMENTS

| 5,080,589 A | 1/1992 | Odén et al. |
| 5,687,788 A * | 11/1997 | Caldarise et al. ............. 164/456 |
| 5,897,592 A | 4/1999 | Caldarise et al. |
| 6,364,663 B1 | 4/2002 | Dinkelacker |

(Continued)

FOREIGN PATENT DOCUMENTS

DE    10 2004 054 875 A1    5/2006

(Continued)

OTHER PUBLICATIONS

Roemmp Chemie Lexikon George Theime Verlag, Stuttgart New York, 9th Edition, 1995 pp. 2190/2191, catchword Keramik.

*Primary Examiner* — Larry Thrower
(74) *Attorney, Agent, or Firm* — Frommer Lawrence & Haug LLP

(57) ABSTRACT

The invention relates to a method for producing implants and components by direct shaping. The method includes the steps of producing a mold for the implants or components to be produced, making allowances for changes in geometry occurring during after-treatment after the implants or components are removed from the mold, and, providing partial areas of the mold with a structured surface for transferring this structure to the surfaces of the implants or components. In the method, raw material is introduced into the mold and, after remaining in the mold for a certain period of time, the hardened raw material is then removed from the mold to allow the implants or components to take on the structured surface of the mold as well as its geometry. The demolded implants or components are finally subjected to any after-treatment that may be necessary.

9 Claims, 1 Drawing Sheet

(56) References Cited

U.S. PATENT DOCUMENTS

2006/0246399 A1    11/2006    Ehrl
2008/0160484 A1    7/2008    Huhn et al.

FOREIGN PATENT DOCUMENTS

| | | |
|---|---|---|
| DE | 10 2005 013 200 | 9/2006 |
| DE | 10 2006 005 034 A1 | 8/2007 |
| EP | 0 375 647 | 6/1990 |
| EP | 1 013 236 B1 | 11/2000 |
| EP | 0 672 395 B1 | 8/2001 |
| EP | 1 797 840 A1 | 6/2007 |
| WO | WO 2005/120386 A1 | 12/2005 |
| WO | WO 2007/090529 | 8/2007 |

* cited by examiner

PROCESS FOR PRODUCING IMPLANTS AND COMPONENTS BY DIRECTING SHAPING

The present application claims priority from PCT Patent Application No. PCT/DE2008/050026 filed on Aug. 13, 2008, which claims priority from German Patent Application No. 10 2007 038958.4 filed on Aug. 15, 2007, the disclosure of which is incorporated herein by reference in its entirety.

BACKGROUND OF THE INVENTION

1. Field of the Invention

The invention is directed to a process for producing implants and components by direct shaping.

2. Description of Related Art

Dental implants in current use mostly have a geometrically defined shape. They are formed of one or more parts. In implants formed of multiple parts, the components connected to the implants likewise have a geometrically defined shape or also partially have a free-form geometry. Frameworks on implant superstructures or components can also partially have a geometrically defined shape or an entirely free-form geometry. The fabrication of implants and components is carried out by computer-aided production methods. An implant comprising multiple parts usually has a complex outer surface which is entirely or partially microstructured for contact with the bone and with the peri-implant soft tissue and has an inner surface which ensures the mechanical connection to the components.

Since one-piece dental implants have the basic disadvantage that they do not allow for the possibility of correcting the fit of a framework once they have been inserted in the jaw, metal dental implants with a superstructure formed of multiple parts (implant and screwed-in or plugged-in components) are predominantly used. The materials chiefly described are titanium or titanium alloys. Ceramic implants of aluminum oxide ceramic or zirconium dioxide ceramic also have been, and continue to be, used. In clinical respects, aluminum oxide ceramic has not proven successful either for dental implants or components. In contrast, the long-term results for frameworks on teeth fabricated from aluminum oxide have been positive. Zirconium dioxide implants are used as one-piece implants (implant and component inseparably connected in one part). Ceramic components, so-called abutments, are fabricated from zirconium dioxide ceramic. The connecting members can be made of metal or ceramic.

Ceramic implants are fabricated by abrasive methods (grinding from zirconium dioxide ceramic). Mechanical machining of ceramics is disadvantageous in that the strength of the ceramic is considerably reduced, even when densesintered and HIPped (HIP: Hot Isostatic Pressing) ceramic was used. Alternatively, production by means of injection molding has been described.

The production of implants by means of injection molding causes microstructures with a high proportion of residual pores which negatively influence the mechanical and biological properties of the implants.

To improve the contact between the outer implant geometry of the metal implants and the jawbone, the metal implants are additively coated or abrasively structured. The aim is to achieve a microstructure which ensures optimal contact between the bone and the implant. Additive coatings are made of inorganic substances, e.g., hydroxylapatite or bio-glasses, or of organic substances, e.g., bioactive substances, e.g., growth factors or polylactides. Abrasive structuring methods include blasting with aluminum oxide particles or etching with acids or caustic solutions, and possibly also combinations of these two methods.

For the treatment of patients with implant-supported dental restorations, the optimal implant position in the jaw and the position of the components and framework can be determined based on data of imaging data acquisition systems (computer tomography, digital volume tomography) and/or optical/mechanical digitizing methods. The production of components and frameworks can be carried out based on the data of imaging data acquisition systems (e.g., computer tomography, digital volume tomography) and/or optical/mechanical digitizing methods. Computer-aided methods have mostly been dismissed for routine clinical use. Implants in current use chiefly have standardized geometries.

SUMMARY OF THE INVENTION

It is the object of the invention to provide a possibility for producing implants and/or components while avoiding the disadvantages of the prior art.

According to the invention, this object is met by a process for producing implants or components in that a mold is initially produced for the implants or components to be produced, wherein allowance is made for changes in geometry occurring during after-treatment after the implant or components have been removed from the mold, and, further, at least partial areas of the mold are provided with a structured surface for transferring this structure to the surfaces of the implants or components, in that the raw material is introduced into the mold, in that after remaining in the mold for a certain period of time the hardened raw material is then removed from the mold, wherein the implants or components have taken on the structured surface of the mold as well as its geometry, and in that the demolded implants or components are finally subjected to any after-treatment which might be necessary.

It can be advantageous when the mold is composed of different partial elements, wherein individual portions can be produced from different mold materials. This is particularly advantageous because only certain areas may need to have the structured surface. Accordingly, the structured surface can be produced in particular by using a porous mold material having an inherently rough surface. In a metal mold material, the structured surface would have to be produced by corresponding depressions.

According to the present application, an implant is a medical product which is inserted into the jawbone and which has a defined geometry, in the sense of being standardized, or an individual (free-form) geometry.

According to the present application, a component is anything functioning as a connecting member between the implant and framework. Components can be anchored to an individual implant or to a plurality of implants or in combination with natural teeth.

According to the present application, a mold is any device in which the raw material is inserted partially or all at once. The inner portions of the mold are relevant for shaping the geometry of the molded implant or component. The closed mold can contain openings and channels for filling with the raw material or for the escape of gases (e.g., air or protective gas) contained in the mold.

According to the present application, a partial mold a portion of the mold which is generally formed of more than one part. The sum of all partial molds makes up a closed hollow mold. The spatial allocation of the partial molds is ensured by design.

According to the present application, a mold material is any material from which the partial molds are made and which can be different in individual partial molds (plastic, metal, ceramic, polymer ceramic, mineral substances (e.g., investment materials, plaster of Paris, paraffins). Accordingly, porous mold materials are used for direct shaping methods exclusively or partially.

According to the present application, a geometry is the shape of the implant to be shaped or of the component to be shaped. The geometry of the shaped implants/components must be distinguished from the geometry of the after-treated implants/components.

According to the present application, anything which is undergone by the demolded implant or the demolded component in processing steps antecedent to its final state and which has an effect on its geometry (e.g., by reacting with the furnace atmosphere during sintering).

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

In the course of producing implants and components by direct shaping, molds or partial molds which together make up a mold are produced from mold materials. The changes in geometry of the shaped implants/components occurring during the after-treatment are taken into account. Raw materials (e.g., ceramic slip or metal slip for slip casting or powder for pressing methods) are introduced into the molds either partially or all at once.

Alternatively, partial molds can be filled with ceramic slip or metal slip or powder and are then completed by the absent partial molds to form the complete mold. Raw materials can still be introduced into the completed mold. Slips of different compositions, e.g., 100% yttrium-stabilized zirconium dioxide or a mixture of 50% to 90% yttrium-stabilized zirconium dioxide and 50% to 10% aluminum oxide, are produced by a stirrer bead mill. The raw materials used for this purpose can have different particle sizes (e.g., d=40 nm to 1 µm). By adding organic auxiliary agents, they are dispersed and the rheology is adjusted in such a way that they can be added to a mold whose surface is structured.

Figure 1:
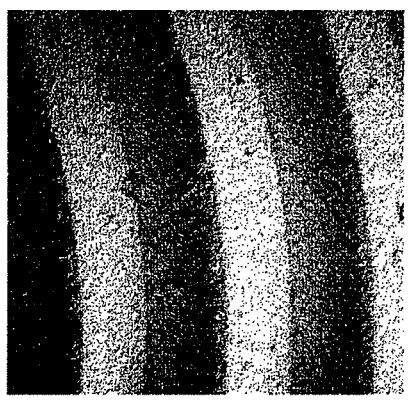
FIG. 1 shows a schematic depiction of a structured surface.
Figure 2:
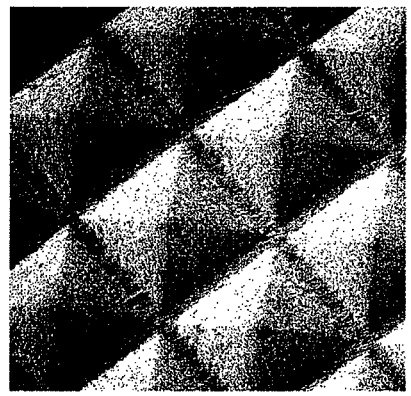
FIG. 2 shows another embodiment of a structured surface of an implant.

Referring to FIGS. 1 and 2, after demolding and sintering, the implants produced in this way have a structured surface characterized by regular raised and depressed portions. Of course, the regular shape of the raised and depressed portions is not at issue. Therefore, according to the invention, a rough surface is already achieved in the process of producing the implant and component for improved growth into the jawbone without any after-treatment. It has been shown that a structured surface has a positive effect on the strength of the connection not only at the contact surfaces between the bone and implant, but also between the components and framework. It is precisely for this reason that the molds for the implants or components are provided with this negative structure at least at the respective eventual contact surfaces for forming this structured surface.

The molds are fabricated individually either corresponding to a standardized geometry of implants or components which are to be produced in series production or in reliance on basic data relating to the jaw and its relevant anatomical adjacent structures (e.g., teeth of both maxilla, soft tissue, muscles), directly on the patient through imaging methods (e.g., photography, x-ray, computer tomography, magnetic resonance tomography, ultrasound, digital volume tomography) or by digitization of the body or body surface or parts of the body or body surface or indirectly by digitization of duplicates of the body or parts thereof (real models) or indirectly by generating corresponding data from measurement data of the body or parts thereof (virtual models). In both cases, allowance is made for the changes in geometry brought about by the after-treatment by corresponding modifications of the mold. Usually, the changes in the geometry of the shaped implants and components during the after-treatment are determined by computerized simulation methods and are transferred to the CAD-/CAM-ready molds in a corresponding manner.

The components can be shaped in a ready-made manner or so as to be tailored to the individual patient. Beyond recording purely digital data, data relating to the jaw and its relevant anatomical adjacent structures (e.g., adjacent teeth, dental antagonists) can be acquired by conventional casting with casting compounds commonly used in dentistry and subsequent fabrication of (plaster of Paris) models. These real models can then be used for further machining and structuring by noncontacting optical and/or mechanical digitization.

By comparing with the digitized data, ready-made components can be selected or, after preparing virtual models, individual components (e.g., abutments, bars, mesostructures) can be fashioned, initially also as virtual models. The individual circumstances relating to tooth gap width, jaw ridge shape and curvature, the dimensions of the existing bone in the area of the implant which is to be inserted or which has already been inserted, and the angulation of the adjacent teeth or implants which are to be taken into account with respect to a component making possible an optimal functional reproduction of the occlusal relations (occlusal contact of the maxillary and mandibular teeth enabling optimal masticatory function, where teeth can also already have been replaced by implants and components or have yet to be replaced) result in an individual or individualized component which is connected to the implant by frictional engagement (e.g., by means of a cone-in-socket connection) or by screwing together with the implant. Screws and threads can be fabricated from metal (e.g., titanium or titanium alloys) and/or ceramic raw materials. Threads can in turn be produced in the mold either partially or all at once by introducing raw materials (e.g., ceramic slip or metal slip for slip casting or powder for pressing methods). Alternatively, partial molds can be filled with ceramic slip or metal slip or powder and the absent partial molds can are added subsequently to form the completed mold. Raw materials can still be introduced into the completed mold.

Components whose individual parts do not come from a completed mold can be connected to the base components by joining techniques (e.g., cementing). It should be noted that the joints of the individual parts are not provided with a structured surface according to FIG. 1 or FIG. 2, but rather, like those produced in one piece, are provided with the structured surface only at the interfaces with the framework.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for producing implants or components comprising the steps of:
   (1) providing a mold for implants or components to be produced, wherein allowance is made by modifying the mold for changes in geometry of the implants occurring during after-treatment after the implants or components are removed from the mold;
   (2) providing at least partial areas of the mold with a structured surface for transferring a structure of the structured surface to the surfaces of the implants or components;
   (3) introducing a raw material into the mold which, after remaining in the mold for a certain period of time, becomes a hardened raw material;
   (4) removing the hardened raw material from the mold, wherein the implants or components have taken on the structured surface of the mold as well as the geometry; and
   (5) subjecting the demolded implants or components to an after-treatment.

2. The method according to claim 1;
wherein the mold is composed of partial molds, and the individual partial molds are produced from different or identical mold materials.

3. The method according to claim 1;
wherein the structured surface of the mold is formed by using a porous mold material.

4. The method according to claim 1;
wherein the structured surface of the mold is produced by incorporating depressions.

5. The method according to claim 1;
wherein a ceramic slip is used as the raw material.

6. The method according to claim 5;
wherein a 100 mass % of yttrium-stabilized zirconium dioxide is used as the ceramic slip.

7. The method according to claim 5;
wherein a mixture of 50 to 90 mass % of yttrium-stabilized zirconium dioxide and 50 to 10 mass % of aluminum oxide is used as the ceramic slip.

8. The method according to claim 1;
wherein a metal slip is used as the raw material.

9. The method according to claim 1;
wherein a powder is used as the raw material in a pressing method.

* * * * *

UNITED STATES PATENT AND TRADEMARK OFFICE
CERTIFICATE OF CORRECTION

| | |
|---|---|
| PATENT NO. | : 9,034,225 B2 |
| APPLICATION NO. | : 12/673101 |
| DATED | : May 19, 2015 |
| INVENTOR(S) | : Baerbel Voigtsberger et al. |

It is certified that error appears in the above-identified patent and that said Letters Patent is hereby corrected as shown below:

Title page (54) Title and in the specification at column 1, line 1:

The title of the application should be corrected as follows:

-- Process for Producing Implants and Components by Directing Shape --

(73) Assignee:

The Assignee name should be corrected as follows:

-- Fraunhofer-Gesellschaft zur Foerderung der angwandten Forschung e. V. --

Signed and Sealed this
Twenty-ninth Day of March, 2016

Michelle K. Lee
*Director of the United States Patent and Trademark Office*

UNITED STATES PATENT AND TRADEMARK OFFICE
CERTIFICATE OF CORRECTION

PATENT NO. : 9,034,225 B2
APPLICATION NO. : 12/673101
DATED : May 19, 2015
INVENTOR(S) : Baerbel Voigtsberger et al.

Page 1 of 1

It is certified that error appears in the above-identified patent and that said Letters Patent is hereby corrected as shown below:

TITLE Page:

"(73) Assignee:

The Assignee name should be corrected as follows:

-- Fraunhofer-Gesellschaft zur Foerderung der angwandten Forschung e. V. --"

(as corrected to read in the Certificate of Correction issued March 29, 2016) is deleted and patent is returned to its original state with the applicant & assignee name in patent to read --(73) Assignee: Fraunhofer-Gesellschaft zur
Foerderung de angwandten Forschung
e.V, Munich (DE)--

Signed and Sealed this
Fifth Day of July, 2016

Michelle K. Lee
*Director of the United States Patent and Trademark Office*